(12) United States Patent
Wang et al.

(10) Patent No.: US 7,390,549 B2
(45) Date of Patent: Jun. 24, 2008

(54) ASYMMETRIC BIS (INDOLESTYRYL) COMPOUND AND HIGH DENSITY RECORDING MEDIA UTILIZING THE SAME

(75) Inventors: Shin-Shin Wang, Hsinchu (TW); Chii-Chang Lai, Taichung Hsien (TW); Hui-Ping Tsai, Hsinchu (TW); Chien-Liang Huang, Taoyuan County (TW); Wen-Yih Liao, Taichung (TW); Ming-Chia Lee, Taichung Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 580 days.

(21) Appl. No.: 11/154,614

(22) Filed: Jun. 17, 2005

(65) Prior Publication Data

US 2006/0142590 A1    Jun. 29, 2006

(30) Foreign Application Priority Data

Dec. 27, 2004    (TW) .............................. 93140712 A

(51) Int. Cl.
*B32B 3/02* (2006.01)
(52) U.S. Cl. .................. 428/64.1; 428/64.8; 430/270.18
(58) Field of Classification Search ................ 428/64.1, 428/64.4, 64.8; 430/270.14, 270.18
See application file for complete search history.

(56) References Cited

U.S. PATENT DOCUMENTS 6,761,952 B1    7/2004    Lee et al.
6,815,031 B2    11/2004    Huang et al.

FOREIGN PATENT DOCUMENTS

EP    1 130 063 A1    9/2001
EP    1 156 084 A2    11/2001
EP    1 170 339 A2    1/2002
JP    11-034489 A    2/1999

*Primary Examiner*—Elizabeth Mulvaney
(74) *Attorney, Agent, or Firm*—Birch, Stewart, Kolasch & Birch, LLP

(57) ABSTRACT

An asymmetric bis(indolestyryl) compound. The asymmetric bis(indolestyryl) compound has formula (I):

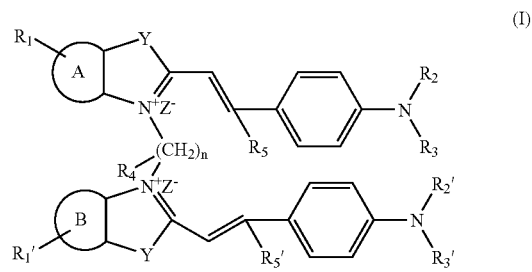

wherein A and B comprise benzene, naphthalene, or heterocyclic ring containing O, S, or N, R1 and R1' are H, halogen atoms, $C_{1-5}$ alkyl, nitro, ester, carboxyl, sulfo, $C_{1-3}$ alkoxy, amine, alkylamine, cyano, $C_{1-6}$ alkylsulfonyl, or $C_{2-7}$ alkoxy carbonyl, $R_2$, $R_2'$, $R_3$, and $R_3'$ comprise H, $C_{1-6}$ alkyl, $C_{6-18}$ aryl, $C_{2-6}$ alkenyl, $C_{3-6}$ cycloalkenyl, or $C_{3-6}$ cycloalkyl, or $C_{3-6}$ cycloalkyl containing hetero atom, $R_4$ is H, hydroxyl, halogen atoms, or alkoxy, $R_5$ and $R_5'$ comprise H, halogen atoms, $C_{1-5}$ alkyl, nitro, $C_{1-3}$ alkoxy, amine, cyano, $C_{1-6}$ alkylsulfonyl, or $C_{2-7}$ alkoxy carbonyl, n is 1~18, Y is $C(R_6R_7)$, $C_{1-3}$ alkylamino or hetero atom, $R_6$ and $R_7$ are $C_{1-3}$ alkyl, and $Z^-$ is an anion or an anionic organometallic complex. The invention also provides a high density recording medium utilizing the asymmetric bis(indolestyryl) compound.

22 Claims, 1 Drawing Sheet

ASYMMETRIC BIS (INDOLESTYRYL) COMPOUND AND HIGH DENSITY RECORDING MEDIA UTILIZING THE SAME

BACKGROUND

The present invention relates to an indolestyryl compound, and more specifically to an asymmetric bis(indolestyryl) compound used in a high density recording medium.

With advances in information and multimedia generation, computer, communication, and consumer (3C) electronic products with increased recording density and capacity, microminiaturization and low cost are required to meet the flow of information. Currently, magnetic recording media have been replaced by high density optical recording media. For optical recording media, improved recording density has been provided by, for example, reduction of wavelength of readout laser such as reduction from red light region to blue, or increase of number aperture (NA). Another important research topic, however, is modification of organic dye structures in optical recording layers. Research has endeavored to develop optical dyes with high solubility, strong absorption in visible light region, photostability, thermal stability, or simple synthesis.

Dyes of CD-R are not suitable for use in high density recording media such as DVD-R due to their different laser wavelengths, CD-R having 780 nm and DVD-R 650 nm. Additionally, related organic dyes in recording layers lack photostability, thermal stability, and simple synthesis, resulting in shorter recording times and higher costs. Thus, development of organic dyes providing improved optical characteristics of high recording media is desirable.

SUMMARY

The invention provides an asymmetric bis(indolestyryl) compound having formula (I):

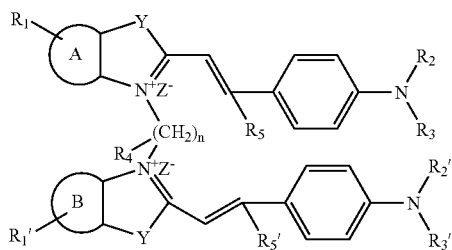

(I)

wherein A and B are the same or different and comprise benzene, naphthalene, or heterocyclic ring containing O, S, or N, $R_1$ and $R_1'$ are H, halogen atoms, $C_{1-5}$ alkyl, nitro, ester, carboxyl, sulfo, $C_{1-3}$ alkoxy, amine, alkylamine, cyano, $C_{1-6}$ alkylsulfonyl, or $C_{2-7}$ alkoxy carbonyl, $R_2$, $R_2'$, $R_3$, and $R_3'$ are the same or different and comprise H, substituted or non-substituted $C_{1-6}$ straight chain or branched alkyl, substituted or non-substituted aryl, $C_{2-6}$ straight chain or branched alkenyl, $C_{3-6}$ cycloalkenyl, or substituted or non-substituted $C_{3-6}$ cycloalkyl, or $C_{3-6}$ cycloalkyl containing hetero atom, $R_4$ is H, hydroxyl, halogen atoms, or alkoxy, $R_5$ and $R_5'$ are the same or different and comprise H, halogen atoms, $C_{1-5}$ alkyl, nitro, $C_{1-3}$ alkoxy, amine, cyano, $C_{1-6}$ alkylsulfonyl, or $C_{2-7}$ alkoxy carbonyl, n is 1~18, Y is $C(R_6R_7)$, $C_{1-3}$ alkylamino or hetero atom, $R_6$ and $R_7$ are $C_{1-3}$ alkyl, and $Z^-$ is an anion or an anionic organometallic complex, and wherein, when A=B, $R_1$ is not equal to $R_1'$ and when A≠B, $R_1$ is equal to $R_1'$ or not, and $R_2$ and $R_3$ or $R_2'$ and $R_3'$ are joined together or with a benzene to form a ring.

The invention also provides a high density recording medium comprising a first substrate, a recording layer formed thereon comprising the disclosed asymmetric bis(indolestyryl) compound, a reflective layer formed on the recording layer, and a second substrate formed on the reflective layer.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION

Figure 1:
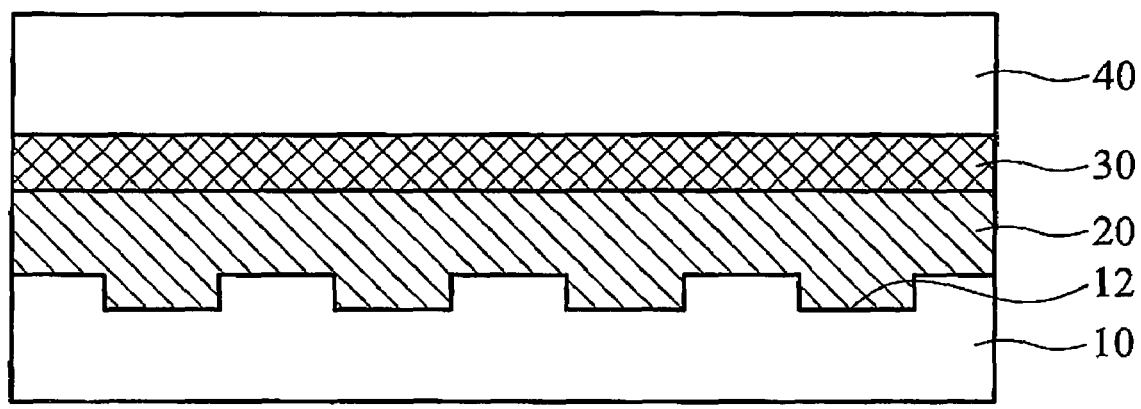
FIG. 1 is a cross section of a high density recording medium of the invention.

The invention provides an asymmetric bis(indolestyryl) compound having formula (I):

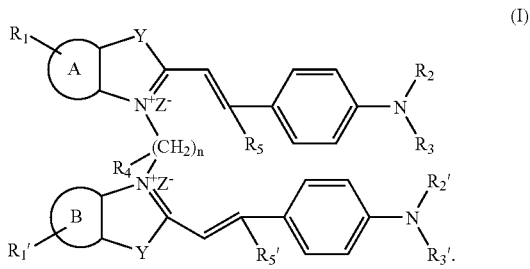

(I)

In formula (I), A and B are the same or different such as benzene, naphthalene, and heterocyclic ring containing O, S, or N, such as furan, pyrazine, pyrrole, pyrazole, pyridazine, pyridine, pyridone, pyrimidine, thiazole, thiophene, quinine, and isoquinine. $R_1$ and $R_1'$ comprise H, halogen atoms, $C_{1-5}$ alkyl, nitro, ester, carboxyl, sulfo, $C_{1-3}$ alkoxy, amine, alkylamine, cyano, $C_{1-6}$ alkylsulfonyl, or $C_{2-7}$ alkoxy carbonyl. When A=B, $R_1$ is not equal to $R_1'$, and when A≠B, $R_1$ is equal to $R_1'$ or not, $R_2$, $R_2'$, $R_3$, and $R_3'$ are the same or different such as H, substituted or non-substituted $C_{1-6}$ straight chain or branched alkyl, substituted or non-substituted $C_{6-18}$ aryl, $C_{2-6}$ straight chain or branched alkenyl, $C_{3-6}$ cycloalkenyl, or substituted and non-substituted $C_{3-6}$ cycloalkyl or $C_{3-6}$ cycloalkyl containing hetero atom. $R_2$ and $R_3$ or $R_2'$ and $R_3'$ may be joined together or with a benzene to form a ring. Substituted groups in $R_2$, $R_2'$, $R_3$, and $R_3'$ comprise halogen atoms, nitro, cyano, hydroxyl, carboxyl, ester, sulfo, sulfoate, or sulfamide. $R_4$ may comprise H, hydroxyl, halogen atoms, or alkoxy. $R_5$ and $R_5'$ are the same or different such as H, halogen atoms, $C_{1-5}$ alkyl, nitro, $C_{1-3}$ alkoxy, amine, cyano, $C_{1-6}$ alkylsulfonyl, and $C_{2-7}$ alkoxy carbonyl. Y is $C(R_6R_7)$, $C_{1-3}$ alkylamino or hetero atom, wherein $R_6$ and $R_7$ are $C_{1-3}$ alkyl. $Z^-$ is an anion or an anionic organometallic complex such as halogen atoms, $ClO_4^-$, $BF_4^-$, $PF_6^-$, $BPh_4^-$, $SbF_6^-$, tetracyano p-quinodimethane ($TCNQ^-$), tetracyano ethylene ($TCNE^-$), and benzene sulfonate, and n is 1~18.

The asymmetric bis(indolestyryl) compound has an absorbing wavelength of about 400~700 nm, an absorbing coefficient (ε) exceeding $10^5$, and a solubility exceeding 2% in organic solvent such as $C_{1-6}$ alcohol, $C_{1-6}$ ketone, $C_{1-8}$ ether, halide, and amide.

The asymmetric bis(indolestyryl) compounds provided by the invention comprise
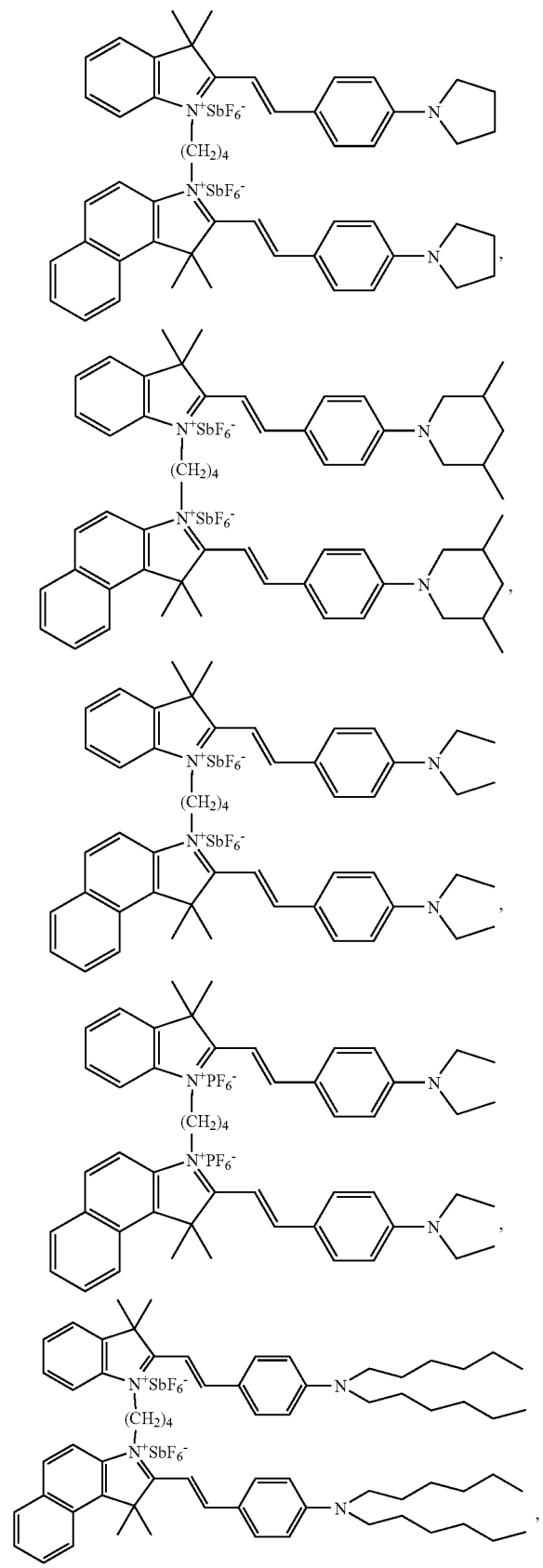
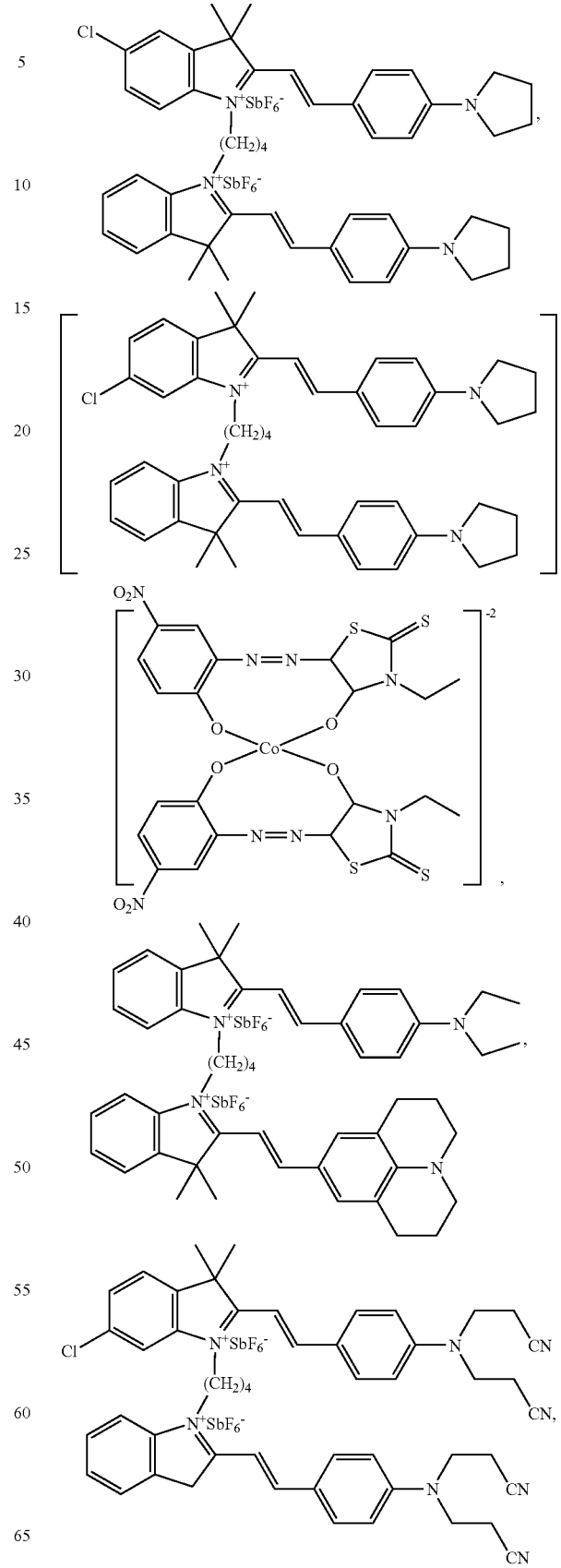

-continued

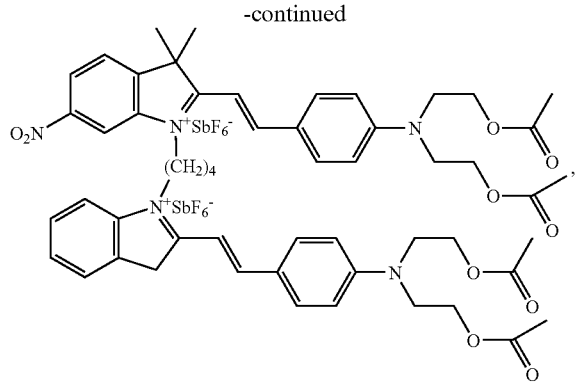

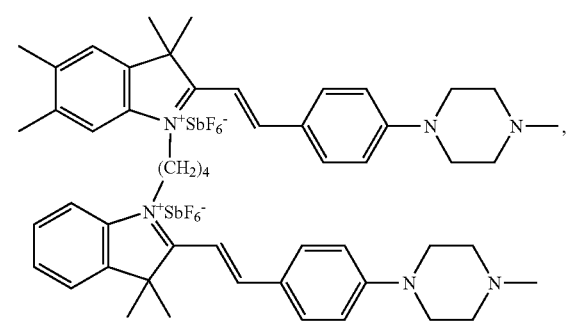

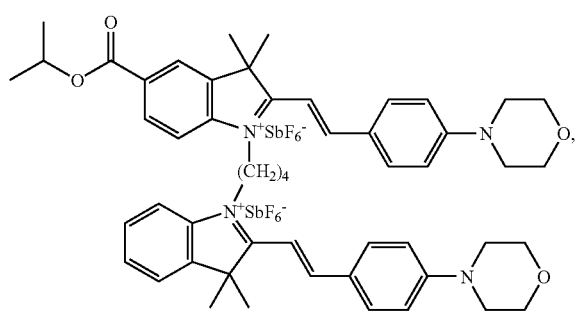

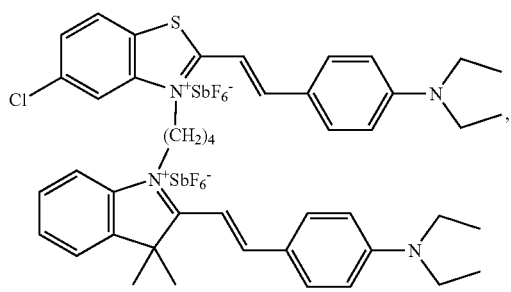

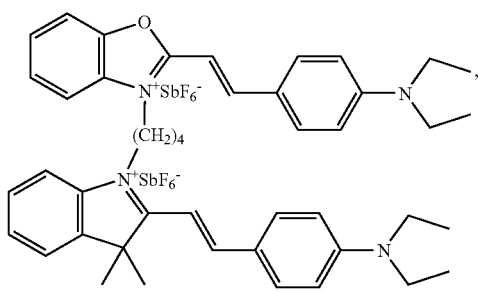

-continued

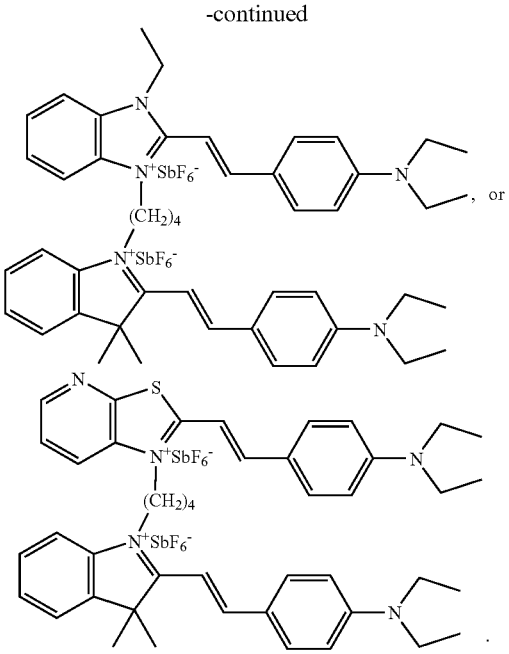

The compound of formula (I) is prepared as follows. First, an asymmetric bis-indole compound such as

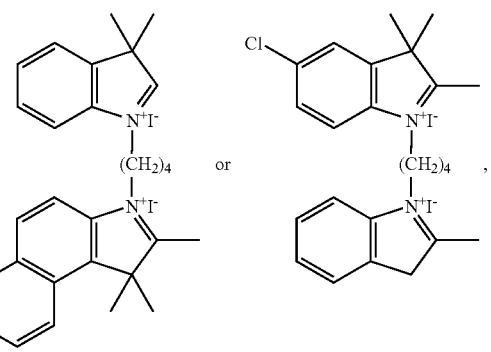

solvent such as ethanol or methanol, and benzaldehyde such as p-N,N-diethyl benzaldehyde or p-N,N-dihexyl benzaldehyde, are added to a flask and reacted at 80~100° C. for 20~24 hours. An asymmetric bis(indolestyryl) compound is prepared after extracting solvent. The asymmetric bis(indolestyryl) compound, solvent such as methanol or ethanol, and a metal salt are added to a flask and reacted at 80~100° C. for 1~2 hours. The metal salt comprises Li, Na, or K salt such as $NaSbF_6$ or $NaPF_6$. After cooling to room temperature and filtration, an asymmetric bis(indolestyryl) compound provided by the invention is prepared.

The invention also provides a high density recording medium comprising a first substrate, a recording layer formed thereon comprising the disclosed asymmetric bis(indolestyryl) compound, a reflective layer formed on the recording layer, and a second substrate formed on the reflective layer.

The first and second substrates are transparent substrates having trenches and comprise polyester, polycarbonate, or polyolefin. The recording layer has a thickness of about 50~300 nm and comprises asymmetric bis(indolestyryl), cyanine dye or azo metal chelate compounds. The asymmetric bis(indolestyryl) compound and cyanine dye or azo metal chelate compounds have a weight ratio of about 100:0~1:99. The reflective layer comprises Au, Ag, Al, Cu, Cr, or alloys thereof.

The high density recording medium has a reflectance of about 40~60%, preferably 52%, a jitter of about 8.5~10.5, preferably 8.7, and a modulation of about 0.6~0.7, preferably 0.69. The high density recording medium comprises a Digital Versatile Disk-Recordable (DVD-R).

A method of fabricating a high density recording medium is further provided. A first substrate is provided and a solution containing an asymmetric bis(indolestyryl) compound and solvent is prepared simultaneously. The solvent may comprises $C_{1-6}$ alcohol, $C_{1-6}$ ketone, $C_{1-8}$ ether, dibutyl ether (DBE), halide, or amide. The $C_{1-6}$ alcohol comprises methanol, ethanol, isopropanol, diaceton alcohol (DAA), 2,2,3,3-tetrafluoropropanol (TFP), trichloroethanol, 2-chloroethanol, octafluoropentanol, or hexafluorobutanol. The $C_{1-6}$ ketone comprises acetone, methyl isobutyl ketone (MIBK), methyl ethyl ketone (MEK), or 3-hydroxy-3-methyl-2-butanone. The halide comprises chloroform, dichloromethane, or 1-chlorobutane. The amide comprises dimethyl formamide (DMF), dimethyl acetamide (DMA), or methyl cyclohexane (MCH). The solution is then coated on the first substrate and dried to form a recording layer, utilizing spin coating, vacuum deposition, spray coating, immersion coating, stick coating, fluid coating, printing coating, or tape coating, preferably spin-coating. Next, a reflective layer is evaporated on the recording layer. Finally, a second substrate is bonded to the reflective layer to form a high density recording medium. A protection layer may be coated on the reflective layer before the second substrate is bonded.

EXAMPLES

Example 1

Preparation of Compound 1

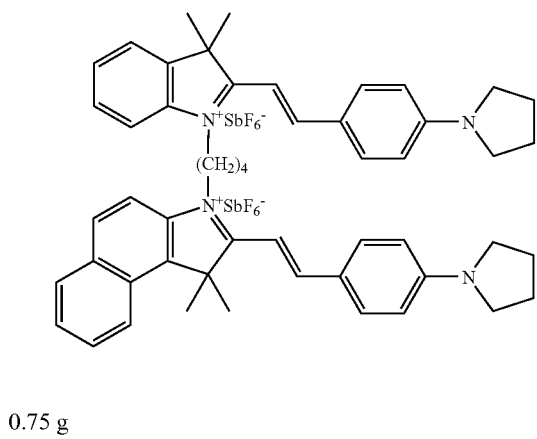

0.75 g

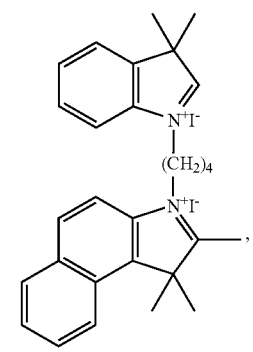

0.4 g

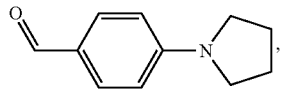

and ethanol were added to a 50 ml flask with thermal reflux overnight.

0.95 g

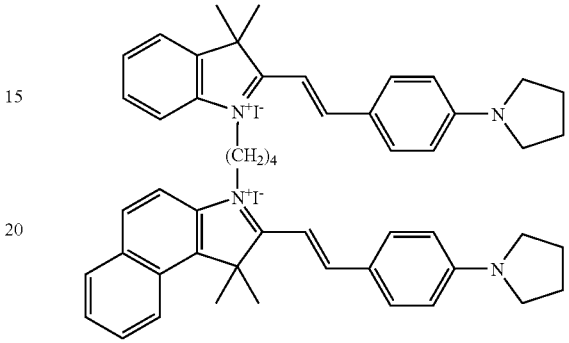

was obtained. 0.95 g

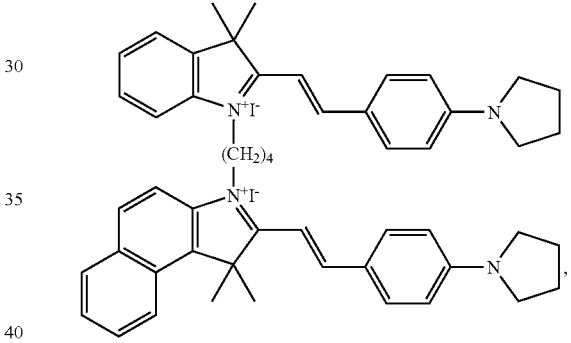

ethanol, and 0.75 g $NaSbF_6$ were added to a 50 ml flask with thermal reflux overnight. After cooling to room temperature and filtration, 1.04 g compound 1 was prepared with yield of 89.4%.

Example 2

Preparation of Compound 4

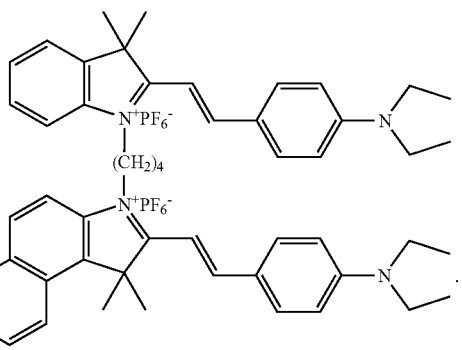

2 g

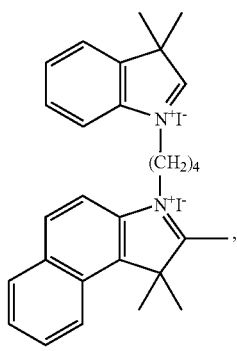

1.1 g

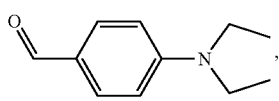

and ethanol were added to a 50 ml flask with thermal reflux overnight. 2.85 g green

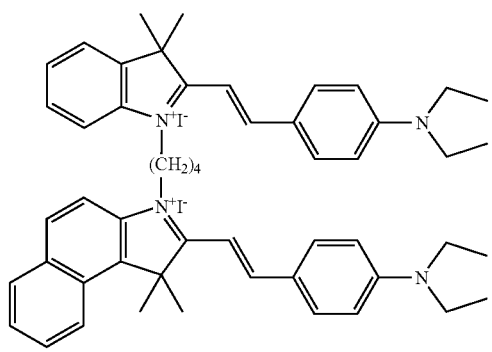

was obtained. 1.69 g

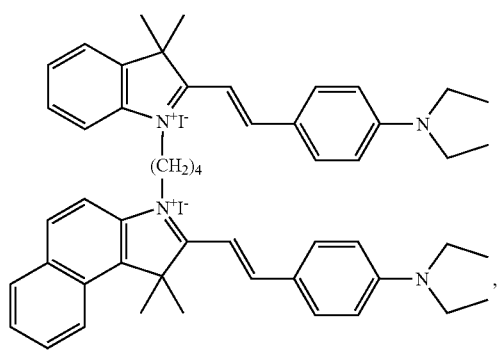

ethanol, and 0.63 g NaSbF$_6$ were added to a 50 ml flask with thermal reflux overnight. After cooling to room temperature and filtration, 1.46 g blue color compound 4 was prepared with yield of 83.5%.

Example 3

Preparation of Compound 5

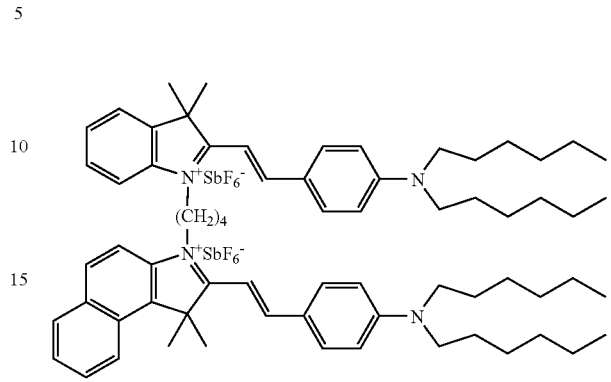

2.52 g

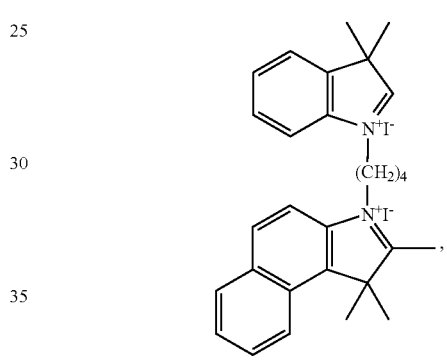

2.29 g

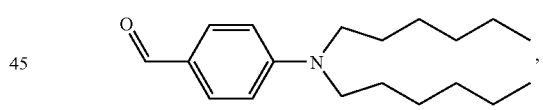

and ethanol were added to a 50 ml flask with thermal reflux over night. 4.9 g

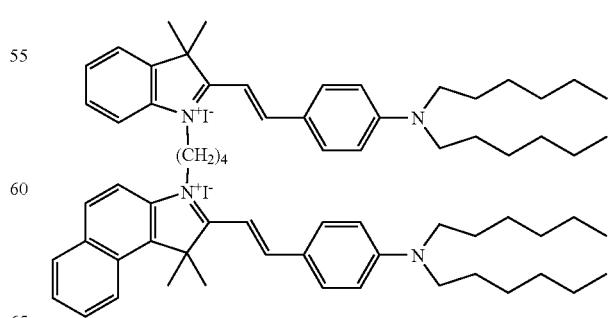

was obtained. 2.45 g

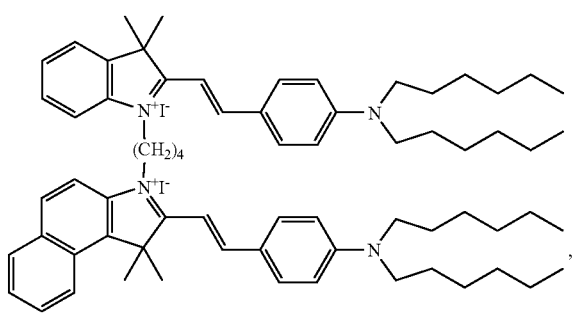

ethanol, and 1.15 g NaSbF$_6$ were added to a 50 ml flask with thermal reflux overnight. After cooling to room temperature and filtration, 1.68 g compound 5 was prepared with yield of 62.4%.

Six asymmetric bis(indolestyryl) compounds (compound 1~6) were prepared, with absorbing wavelengths (nm) and absorbing coefficient ($\epsilon$) as shown in Table 1.

TABLE 1

| Compound number | Structure | Absorbing wavelength (nm) | Absorbing coefficient ($\epsilon$) |
|---|---|---|---|
| Compound 1 | 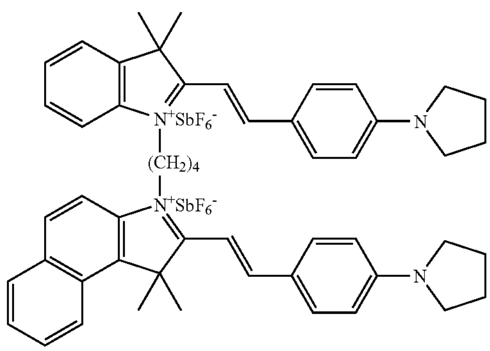 | 561 | $1.77 * 10^5$ |
| Compound 2 | 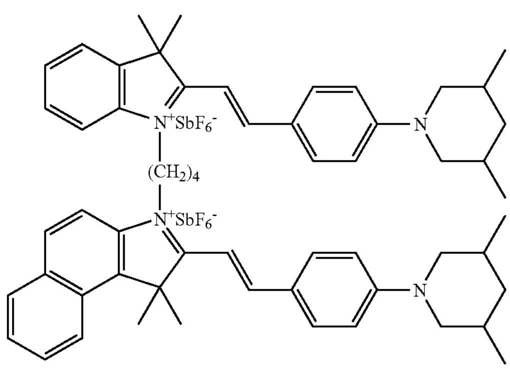 | 561 | $1.5 * 10^5$ |
| Compound 3 | 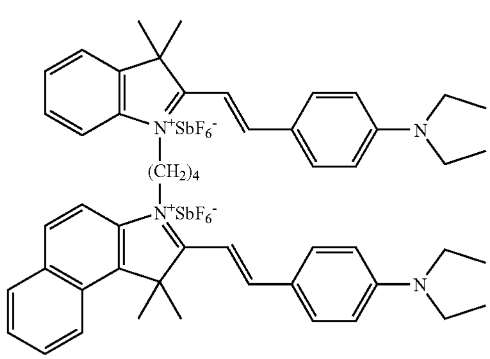 | 557 | $1.62 * 10^5$ |

TABLE 1-continued

| Compound number | Structure | Absorbing wavelength (nm) | Absorbing coefficient (ε) |
|---|---|---|---|
| Compound 4 | 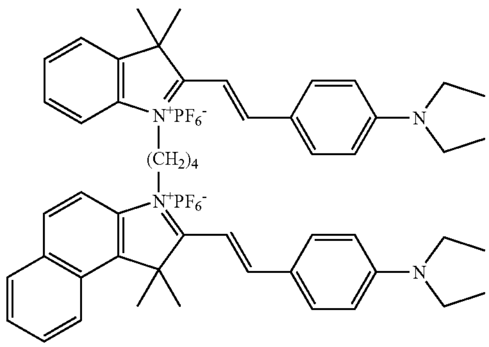 | 556 | $1.97 * 10^5$ |
| Compound 5 | 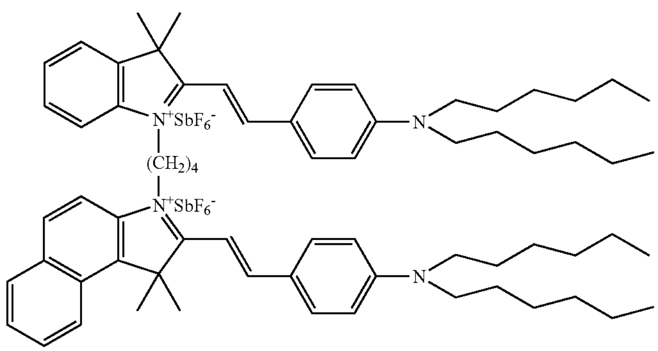 | 562 | $1.84 * 10^5$ |
| Compound 6 | 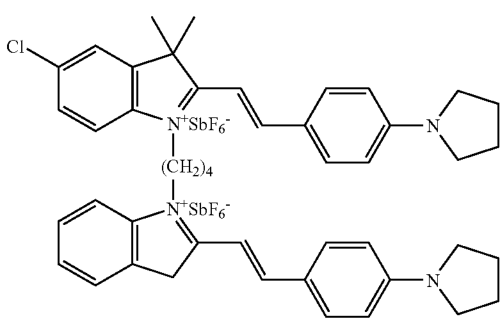 | 564 | $1.71 * 10^5$ |

Example 4

Fabrication of High Density Recording Medium (1)

Referring to FIG. 1, a method of fabricating a high density recording medium is disclosed according to the following example, in which a polycarbonate first substrate 10 at a diameter of 120 mm and a thickness of 1.2 mm having trenches 12 at a depth of 130 nm and a width of 300 nm was provided. A solution (1.7 wt %) containing a compound 3 and 2,2,3,3-tetrafluoropropanol (TFP) was prepared simultaneously. Next, the solution was coated on the first substrate 10 by spin coating and dried at 80° C. for 5 min to form a recording layer 20. An Ag layer was then sputtered on the recording layer 20 to form a reflective layer 30 at a thickness of 200 nm. Finally, a second substrate 40 was bonded to the reflective layer 30 to form a high density recording medium.

A UV resin was coated on the reflective layer 30 to form a protective layer of about 10 μm (not shown) before the second substrate 40 was bonded.

Example 5

Fabrication of High Density Recording Medium (2)

Referring to FIG. 1, a method of fabricating another high density recording medium is disclosed according to the following example, in which a polycarbonate first substrate 10 at a diameter of 120 mm and a thickness of 1.2 mm having trenches 12 at a depth of 130 nm and a width of 300 nm was provided. A solution (1.7%) containing a compound 4, cyanine dye of 0~99% weight ratio, and 2,2,3,3-tetrafluoropropanol (TFP) was prepared simultaneously. Next, the solution was coated on the first substrate 10 by spin coating and dried at 80° C. for 5 min to form a recording layer 20 at a thickness of 200 nm. An Ag layer was then sputtered on the recording layer 20 to form a reflective layer 30 at a thickness of 200 nm. Finally, a second substrate 40 was bonded to the reflective layer 30 to form a high density recording medium. A UV resin was coated on the reflective layer 30 to form a protective layer of about 10 μm (not shown) before the second substrate 40 was bonded.

Reflectance, jitter, and modulation of high density recording media (1) and (2) were shown in Table 2.

TABLE 2

|  | Reflectance (%) | Jitter | Modulation |
|---|---|---|---|
| High density recording medium (1) | 45.1 | 10.1 | 0.688 |
| High density recording medium (2) | 52.7 | 8.71 | 0.603 |

The results indicate that the high density recording media with modified recording layers of the invention provides better photoelectrical performance. Reflectance, jitter, and modulation of related products are 45%, 8.0, and 0.6, respectively. Additionally, these media also provide high recording sensitivity and high carrier-to-noise ratio (CNR).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An asymmetric bis(indolestyryl) compound having formula (I):

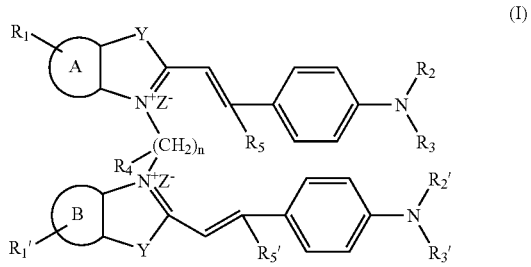

wherein A and B are the same or different and comprise benzene, naphthalene, or heterocyclic ring containing O, S, or N, $R_1$ and $R_1'$ are H, halogen atoms, $C_{1-5}$ alkyl, nitro, ester, carboxyl, sulfo, $C_{1-3}$ alkoxy, amine, alkylamine, cyano, $C_{1-6}$ alkylsulfonyl, or $C_{2-7}$ alkoxy carbonyl, $R_2$, $R_2'$, $R_3$, and $R_3'$ are the same or different and comprise H, substituted or non-substituted $C_{1-6}$ straight chain or branched alkyl, substituted or non-substituted $C_{6-18}$ aryl, $C_{2-6}$ straight chain or branched alkenyl, $C_{3-6}$ cycloalkenyl, or substituted or non-substituted $C_{3-6}$ cycloalkyl, or $C_{3-6}$ cycloalkyl containing hetero atom, $R_4$ is H, hydroxyl, halogen atoms, or alkoxy, $R_5$ and $R_5'$ are the same or different and comprise H, halogen atoms, $C_{1-5}$ alkyl, nitro, $C_{1-3}$ alkoxy, amine, cyano, $C_{1-6}$ alkylsulfonyl, or $C_{2-7}$ alkoxy carbonyl, n is 1~18, Y is $C(R_6R_7)$, $C_{1-3}$ alkylamino or hetero atom, $R_6$ and $R_7$ are $C_{1-3}$ alkyl, and $Z^-$ is an anion or an anionic organometallic complex, wherein when A=B, $R_1$ is not equal to $R_1'$ and when A≠B, $R_1$ is equal to $R_1'$ or not, and $R_2$ and $R_3$ or $R_2'$ and $R_3'$ are joined together or with a benzene to form a ring.

2. The asymmetric bis(indolestyryl) compound as claimed in claim 1, wherein A and B comprise furan, pyrazine, pyrrole, pyrazole, pyridazine, pyridine, pyridone, pyrimidine, thiazole, thiophene, quinine, or isoquinine.

3. The asymmetric bis(indolestyryl) compound as claimed in claim 1, wherein substituted groups in $R_2$, $R_2'$, $R_3$, and $R_3'$ comprise H, halogen atoms, alkyl, alkyl halide, nitro, cyano, hydroxyl, carboxyl, ester, sulfo, sulfoate, sulfamide, morpholine, julolidine, or piperazine.

4. The asymmetric bis(indolestyryl) compound as claimed in claim 1, wherein $Z^-$ comprises halogen atoms, $ClO_4^-$, $BF_4^-$, $PF_6^-$, $BPh_4^-$, $SbF_6^-$, tetracyano p-quinodimethane ($TCNQ^-$), tetracyano ethylene ($TCNE^-$), benzene sulfonate, or anionic organometallic complex.

5. The asymmetric bis(indolestyryl) compound as claimed in claim 1, wherein the asymmetric bis(indolestyryl) compound comprises

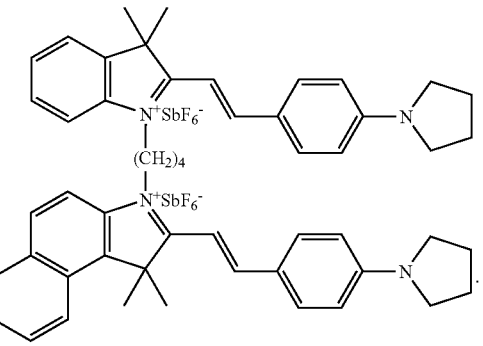

6. The asymmetric bis(indolestyryl) compound as claimed in claim 1, wherein the asymmetric bis(indolestyryl) compound comprises

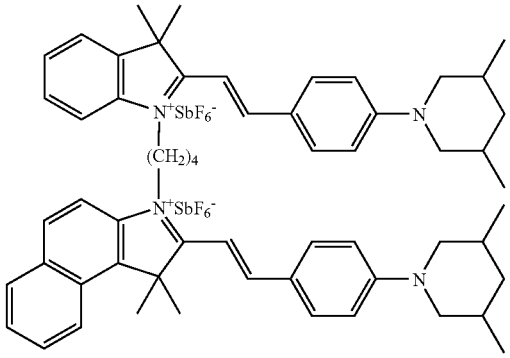

7. The asymmetric bis(indolestyryl) compound as claimed in claim 1, wherein the asymmetric bis(indolestyryl) compound comprises

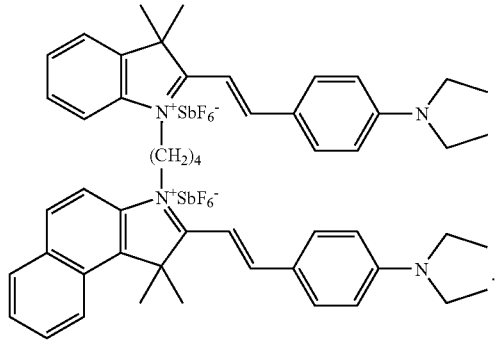

8. The asymmetric bis(indolestyryl) compound as claimed in claim 1, wherein the asymmetric bis(indolestyryl) compound comprises

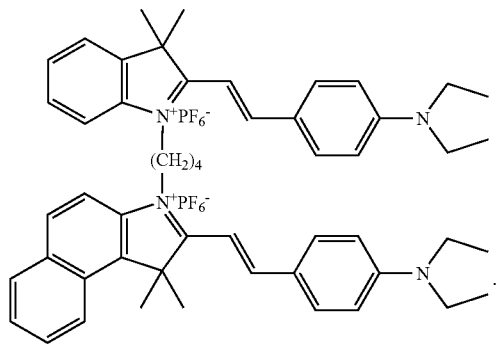

9. The asymmetric bis(indolestyryl) compound as claimed in claim 1, wherein the asymmetric bis(indolestyryl) compound comprises

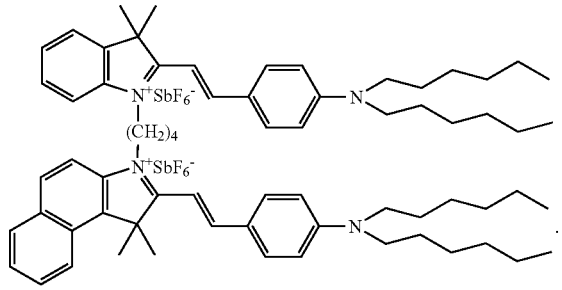

10. The asymmetric bis(indolestyryl) compound as claimed in claim 1, wherein the asymmetric bis(indolestyryl) compound comprises

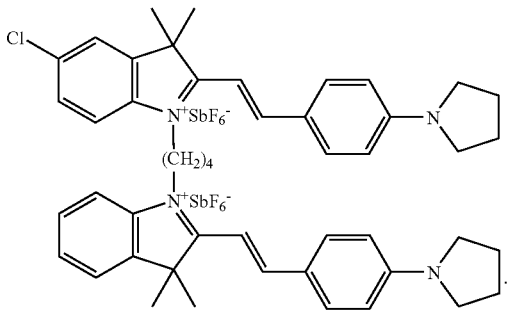

11. The asymmetric bis(indolestyryl) compound as claimed in claim 1, wherein the asymmetric bis(indolestyryl) compound has an absorbing wavelength of about 400~700 nm.

12. The asymmetric bis(indolestyryl) compound as claimed in claim 1, wherein the asymmetric bis(indolestyryl) compound has an absorbing coefficient ($\epsilon$) exceeding $10^5$.

13. The asymmetric bis(indolestyryl) compound as claimed in claim 1, wherein the asymmetric bis(indolestyryl) compound has solubility exceeding 2% in organic solvent.

14. The asymmetric bis(indolestyryl) compound as claimed in claim 13, wherein the organic solvent comprises $C_{1-6}$ alcohol, $C_{1-6}$ ketone, $C_{1-8}$ ether, halide, or amide.

15. A high density recording medium, comprising:
   a first substrate;
   a recording layer formed on the first substrate comprising an asymmetric bis(indolestyryl) compound as claimed in claim 1;
   a reflective layer formed on the recording layer; and
   a second substrate formed on the reflective layer.

16. The high density recording medium as claimed in claim 15, wherein the first and second substrates are transparent substrates having trenches.

17. The high density recording medium as claimed in claim 15, wherein the first and second substrates comprise polyester, polycarbonate, or polyolefin.

18. The high density recording medium as claimed in claim 15, wherein the recording layer comprises cyanine dye or azo metal chelate compounds.

19. The high density recording medium as claimed in claim 18, wherein the asymmetric bis(indolestyryl) compound and cyanine dye or azo metal chelate compounds have a weight ratio of about 1:99~99.9:0.1.

20. The high density recording medium as claimed in claim 15, wherein the reflective layer comprises Au, Ag, Al, Cu, Cr, or alloys thereof.

21. The high density recording medium as claimed in claim 15, wherein the high density recording medium has a reflectance exceeding 45%, a jitter of about 7.5-10.5, and a modulation of about 0.6~0.8.

22. The high density recording medium as claimed in claim 15, wherein the high density recording medium comprises a High Density Digital Versatile Disk-Recordable (DVD-R).

* * * * *